United States Patent

Oeckl et al.

[11] Patent Number: 4,647,687
[45] Date of Patent: Mar. 3, 1987

[54] HALOGENATED SULPHIDES, PROCESS FOR THEIR PREPARATION AND THEIR USE IN MICROBICIDAL AGENTS

[75] Inventors: Siegfried Oeckl, Bergisch-Gladbach; Gerold Schade, Cologne; Hans-Georg Schmitt, Leverkusen; Wilfried Paulus; Hermann Genth, both of Krefeld, all of Fed. Rep. of Germany

[73] Assignee: Bayer Aktiengesellschaft, Leverkusen, Fed. Rep. of Germany

[21] Appl. No.: 678,450

[22] Filed: Dec. 5, 1984

[30] Foreign Application Priority Data

Dec. 24, 1983 [DE] Fed. Rep. of Germany ....... 3346947

[51] Int. Cl.$^4$ ............................................. C07C 121/30
[52] U.S. Cl. ...................................... 558/439; 71/67; 558/438; 562/594; 564/198
[58] Field of Search ................. 260/465.7; 514/526; 558/438, 439; 71/67

[56] References Cited

U.S. PATENT DOCUMENTS

| | | | |
|---|---|---|---|
| 2,469,317 | 5/1949 | Shokal et al. ................. | 514/547 X |
| 2,762,836 | 9/1956 | Selcer .......................... | 260/465.8 |
| 2,993,037 | 7/1961 | Heininger et al. ............ | 260/125 |
| 3,148,109 | 9/1964 | Miller ........................... | 514/547 |
| 4,079,148 | 3/1978 | Oeckl et al. .................. | 260/465.7 X |
| 4,238,405 | 12/1980 | Felix ............................ | 260/465.7 X |
| 4,359,429 | 11/1982 | Mathias et al. .............. | 260/465.8 R X |
| 4,389,400 | 6/1983 | Ho ................................ | 260/465.8 R X |
| 4,424,167 | 1/1984 | Oeckl ........................... | 260/465.7 X |
| 4,438,282 | 3/1984 | Lardon et al. ................ | 260/465.7 X |

FOREIGN PATENT DOCUMENTS 0001312 4/1979 European Pat. Off. .

OTHER PUBLICATIONS

Hasserodt; Chem. Ber., 100, pp. 1482-1490, (1967).

*Primary Examiner*—Joseph Paul Brust
*Attorney, Agent, or Firm*—Sprung Horn Kramer & Woods

[57] ABSTRACT

The new halogenated sulphides of the formula

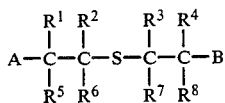

in which $R^1$ to $R^8$ are identical or different and denote hydrogen or halogen, at least one of the radicals $R^1$ to $R^8$ representing halogen, and wherein $R^1$ and $R^2$, and/or $R^3$ and $R^4$ can optionally form an olefinic bond, and A and B are identical or different and denote nitrile, carboxyl, carboxylate or carboxamide, can be prepared by halogenation of bis-(cyanoethyl) sulphide, or by splitting off hydrogen halide from a halogenated bis-(cyanoethyl) sulphide, or by reacting 3-halogeno-acrylonitriles with sulphides. The new compounds can be active compounds in microbicidal agents.

4 Claims, No Drawings

HALOGENATED SULPHIDES, PROCESS FOR THEIR PREPARATION AND THEIR USE IN MICROBICIDAL AGENTS

The invention relates to new halogenated sulphides, processes for their preparation and their use in microbicidal agents.

New halogenated sulphides of the formula

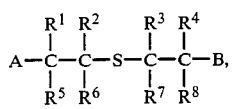

in which
$R^1$ to $R^8$ are identical or different and denote hydrogen or halogen, at least one of the radicals $R^1$ to $R^8$ representing halogen,
and wherein
$R^1$ and $R^2$, and/or $R^3$ and $R^4$ can optionally form an olefinic bond, and
A and B are identical or different and denote nitrile, carboxyl, carboxylate or carboxamide,
have been found.

Where possible, the new compounds can be in the form of their various stereoisomers.

According to the invention, halogen denotes chlorine, bromine or iodine, preferably chlorine or bromine; chlorine is particularly preferred.

Carboxyl in the context of the present invention is understood as the group —COOH.

Carboxylate in the context of the present invention is understood as the group —COOM, in which M can in general denote an alkali metal (for example sodium or potassium), an alkaline earth metal (for example magnesium or calcium) or ammonium.

Carboxamide in the context of the present invention is understood as meaning the group —CONH$_2$.

According to the invention, preferred halogenated sulphides in the context of the formula I are compounds of the formula

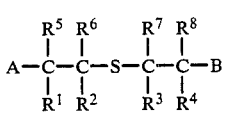

in which
$R^{3'}$ to $R^{8'}$ are identical or different and denote hydrogen, chlorine or bromine,
and wherein
at least one of the radicals $R^{3'}$ to $R^{8'}$ represents chlorine or bromine,
and wherein
$R^{3'}$ and $R^{4'}$ can optionally form an olefinic bond, and
A and B are identical or different and denote nitrile, carboxyl, carboxylate or carboxamide.

According to the invention, particularly preferred halogenated sulphides are those of the formula

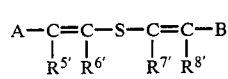

in which $R^{5'}$ to $R^{8'}$, A and B have the abovementioned meaning.

Halogenated sulphides of the formula (III) in which A and B represent nitrile groups and in which halogen denotes chlorine are especially preferred.

The following halogenated sulphides may be mentioned as examples: 1-chloro-2-cyano-vinyl 2-cyano-ethyl sulphide, 1,2-dichloro-2-cyano-vinyl 2-cyano-ethyl sulphide, 1-chloro-2-cyano-vinyl 2,2-dichloro-2-cyano-ethyl sulphide, 1,2-dichloro-2-cyano-vinyl 2,2-dichloro-2-cyanoethyl sulphide, 1,2-dichloro-2-cyano-vinyl 2-chloro-2-cyano-vinyl sulphide, bis-(2-chloro-2-cyano-vinyl) sulphide, bis-(1,2,2-trichloro-2-cyano-ethyl) sulphide, bis(1,2-dichloro-2-cyano-vinyl) sulphide, 2-bromo-2-cyano-vinyl 2-cyano-ethyl sulphide, 2-bromo-1-chloro-2-cyano-vinyl 2-cyano-ethyl sulphide, 2,2-dichloro-3(1,2-dichloro-2-cyano-vinyl)thiopropionic acid amide and 2,2-dichloro-3(1,2-dichloro-2-cyano-vinyl)thio-propionic acid and the sodium salt thereof.

Several processes have been found for the preparation of the new halogenated sulphides.

A process has thus been found for the preparation of halogenated sulphides of the formula

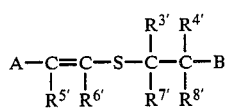

in which
$R^1$ to $R^8$ are identical or different and denote hydrogen or halogen, at least one of the radicals $R^1$ to $R^8$ representing halogen,
and wherein
$R^1$ and $R^2$, and/or $R^3$ and $R^4$ optionally form an olefinic bond, and
A and B are identical or different and denote nitrile, carboxyl, carboxylate or carboxamide,
which is characterized in that bis-(cyanoethyl) sulphide is reacted with a halogenating agent, if appropriate in the presence of an acid-binding agent, and the mixture is then worked up in a manner which is known per se.

The process according to the invention can be illustrated by the following equation:

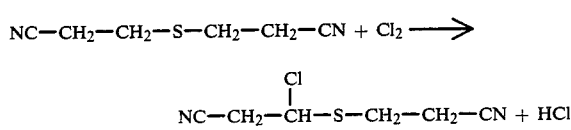

Both saturated and unsaturated halogenated sulphides according to the invention are obtained by the process according to the invention. A mixture of various compounds is in most cases obtained. The pure compounds are easily obtained from the mixture by separation methods which are known per se, such as crystallization, gas chromatography, liquid chromatography, thin layer chromatography or distillation.

The free halogens, such as chlorine, bromine and iodine, preferably chlorine or bromine, sulphuryl halides, such as sulphuryl chloride, and phosphorus halides, such as phosphorus pentachlorine, are used as the halogenating agents.

The process according to the invention can be carried out without a solvent or in the presence of solvents which are inert towards the halogenating agent used. Examples of such solvents are lower aliphatic carboxylic acids, such as acetic acid, or chlorohydrocarbons, such as methylene chloride, chloroform, dichloroethane or chlorobenzene. Preferred solvents are dichlorohydrocarbons, such as methylene chloride, 1,2-dichloroethane and dichlorobenzene.

The reaction temperature in the process according to the invention depends on the halogenating agent used and is in general in the range from $-40°$ to $+120°$ C., preferably in the range from $-20°$ C. to $+80°$ C. It may be appropriate to start the process according to the invention at low temperatures and to increase the temperature in the course of the halogenation.

The process according to the invention is in general carried out under normal pressure. However, it is also possible to carry out the process under a reduced or increased pressure (for example in the pressure range from 0.1 to 100 bar).

If appropriate, the process according to the invention can be carried out in the presence of an acid-binding agent. In general, it is advantageous to add acid-binding agents in order to obtain essentially unsaturated halogenated sulphides according to the invention. Examples of acid-binding agents for the process according to the invention are the hydroxides, carbonates, bicarbonates and acetates of alkali metals (for example sodium and potassium) and alkaline earth metals (for example magnesium and calcium).

Acid-binding agents for the process according to the invention can also be aliphatic or aromatic tertiary amines, such as triethylamine, dimethylaniline or ethyldicyclohexylamine, or heterocyclic compounds, such as pyridine or quinoline.

It is of course also possible to use mixtures of the acid-binding agents. In general, according to the invention, they are used in the stoichiometric amount corresponding to the amount of hydrogen halide to be split off. However, it is also possible to use them in more or less than the stoichiometric amount (for example in a ratio of 0.01:1 to 2:1, preferably 0.01:1 to 0.5:1, based on the bis-(cyanoethyl) sulphide).

It may be advantageous to carry out the process according to the invention in the presence of a phase transfer catalyst. Examples of phase transfer catalysts here are tetraalkylammonium salts and tetraalkylphosphonium salts (alkyl representing an alkyl radical with 1 to about 16 carbon atoms) or polyethers (both cyclic and linear long-chain polyethers with the recurring unit [—CH$_2$—CH$_2$—O] being possible).

In a preferred embodiment of the process according to the invention, the bis-(cyanoethyl) sulphide is reacted with the halogenating agent in a first stage, and the acid-binding agent is then added in a second stage.

The degree of halogenation of the new halogenated sulphides according to the invention is in general controlled by the amount of halogenating agent added. According to the invention, equivalent amounts of the halogenating agent are thus added, according to the number of halogens to be introduced.

However, it is also possible to monitor the progress of the reaction by analytical means; possible such means are gas chromatography, liquid chromatography and thin layer chromatography. It is thereby possible to interrupt the reaction after addition of certain amounts of halogenating agents, by which means the halogen content of the products can be controlled.

In another embodiment of the process according to the invention, particularly pure sulphides with a higher degree of halogenation are obtained if unsaturated halogenated sulphides are prepared, according to the invention, in a first step and, if appropriate, another halogen is then also added on in a second step.

The process according to the invention can be carried out batchwise or continuously.

In general, the process according to the invention is carried out by dissolving the starting compounds in any solvent which may be used and adding the corresponding halogenating agent at the reaction temperature according to the invention. The halogenating agent can be added all at once, in portions or continuously; thus, it is frequently advantageous to add gaseous or liquid halogenating agents continuously.

When the reaction has ended, any solvent, excess halogenating agent and acid-binding agent are removed and the product is purified by customary processes, such as distillation and crystallization. It may also be appropriate to free the sulphide halogenated according to the invention from impurities by chromatography.

It is surprising that the process according to the invention can be used for the preparation of the halogenated sulphides according to the invention, since, as is known, carbon-sulphur bonds are very easily split by halogenating agents. (Tetrahedron 38, 2612 et seq (1982)).

New halogenated sulphides according to the invention, of the formula

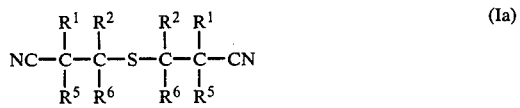

in which

R$^1$, R$^2$, R$^5$ and R$^6$ are identical or different and denote hydrogen or halogen, and wherein at least one of the radicals R$^1$, R$^2$, R$^5$ or R$^6$ represents halogen, and wherein R$^1$ and R$^2$ can optionally form an olefinic bond, can also be prepared by a process in which, in a first reaction step, a sulphide of the formula

in which

Me denotes hydrogen, an alkali metal, an alkaline earth metal or ammonium and n represents the valency of the radical Me, is reacted with 3-halogeno-acrylonitriles of the formula

in which

Hal represents chlorine or bromine and

R$^5$ and R$^6$ have the abovementioned meaning, if appropriate in the presence of a base, the reaction product is then halogenated, if appropriate, in a second reaction step, the product is then reacted with an acid-binding agent, if appropriate, in a third reaction step and the product is then halogenated again, if appropriate, in a fourth reaction step, and the individual reaction steps are worked up, if appropriate, in a manner which is known per se.

In the first stage of the process according to the invention, compounds according to the formula $$NC-\underset{R^5}{\underset{|}{C}}=\underset{R^6}{\underset{|}{C}}-S-\underset{R^6}{\underset{|}{C}}=\underset{R^5}{\underset{|}{C}}-CN \qquad (VI)$$

in which $R^5$ and $R^6$ have the abovementioned meaning, are obtained.

If appropriate, halogen can be added on to these compounds of the formula (VI) in the second reaction stage. Compounds of the formula $$NC-\underset{R^5}{\underset{|}{\underset{|}{C}}}-\underset{R^6}{\underset{|}{\underset{|}{C}}}-S-\underset{R^6}{\underset{|}{\underset{|}{C}}}-\underset{R^5}{\underset{|}{\underset{|}{C}}}-CN \qquad (VII)$$

in which
$R^5$ and $R^6$ have the abovementioned meaning and
$R^9$ represents halogen,
are then obtained.

If $R^5$ or $R^6$ represents hydrogen in the formula (VII), it is possible to split off hydrogen halide in the third reaction step in the presence of an acid-binding agent. Halogenated sulphides according to the invention, with an olefinic bond, are then again obtained.

By adding on halogen again, if appropriate, to the olefinic bond thus formed, perhalogenated compounds according to the invention are obtained.

By this procedure according to the invention, it is possible to obtain compounds containing a mixture of halogen atoms by using different halogens.

The process according to the invention can be illustrated by the following equations:

$$2NC-CCl=CHCl + Na_2S \xrightarrow{-2NaCl}$$
$$NC-CCl=CH-S-CH=CCl-CN$$

$$CN-CCl=CH-S-CH=CCl-CN + 2Cl_2 \longrightarrow$$
$$CN-CCl_2-CHCl-S-CHCl-CCl_2-CN$$

$$CN-CCl_2-CHCl-S-CHCl-CCl_2-CN \xrightarrow{-2HCl}$$
$$CN-CCl=CCl-S-CCl=CCl-CN$$

$$CN-CCl=CCl-S-CCl=CCl-CN + 2Br_2 \longrightarrow$$
$$CN-CClBr-CClBr-S-CClBr-CClBr-CN$$

Surprisingly, it is also possible to combine two or more of the reaction steps in the context of the process according to the invention and to carry them out in the form of a one-pot reaction.

Sulphides which may be mentioned are sulphides and hydrogen sulphides of alkali metals (for example sodium and potassium), alkaline earth metals (for example magnesium and calcium) and ammonium, and hydrogen sulphide.

The 3-halogenoacrylonitriles for the process according to the invention are known per se (Angew. Chemie. 60A, 311 (1948)). They can be prepared, for example, by reacting acrylonitrile with halogenating agents, such as chlorine, if appropriate in the presence of agents which split off hydrogen halide.

The following 3-halogenoacrylonitriles may be mentioned as examples: 2,3-dichloroacrylonitrile, 2,3,3-trichloroacrylonitrile, 2-chloro-3-bromo-acrylonitrile and 2,3-dichloro-3-bromo-acrylonitrile.

In general, the sulphides and the 3-halogenoacrylonitriles are used in approximately stoichiometric amounts.

The reaction is preferably carried out in a solvent which is not changed under the reaction conditions. Possible such solvents are water, aliphatic alcohols, such as methanol and ethanol, ethers, such as diethyl ether and tetrahydrofuran, chlorohydrocarbons, such as methylene chloride and carbon tetrachloride, ketones, such as acetone, esters, such as ethyl acetate, and formamides, such as dimethylformamide.

The process according to the invention is in general carried out in a temperature range from $-20°$ to $+60°$ C., preferably from $0°$ C. to $40°$ C.

The process according to the invention is in general carried out under normal pressure. However, it is also possible to carry out the process under an increased pressure (for example in the pressure range from 1 to 50 bar).

The first reaction step is in general carried out as follows: for the reaction, the reaction components are brought together in solution at the reaction temperature according to the invention. The end of the reaction can be detected by chromatography. The reaction product is worked up by generally customary reaction methods, for example by distillation, crystallization or column chromatography.

It is surprising that the first step of the process according to the invention proceeds with high yields. In particular, it is known that acrylonitriles which carry a halogen in the 2-position form, with sulphides, thiiranes, which react in a very unpredictable manner (J. Org. Chem. 34, 2955 (1969)).

The halogenation in the second and fourth reaction step of the process according to the invention is in general carried out in solution. Inert solvents, such as, for example, $CH_2Cl_2$, $CCl_4$, $ClC_6H_5$ and acetic acid, are advantageously used.

The free halogens, such as chlorine, bromine and iodine, preferably chlorine or bromine, sulphuryl halides, such as sulphuryl chloride, and phosphorus halides, such as phosphorus pentachloride, are used as the halogenating agents.

The halogenation is in general carried out in the temperature range from $-20°$ to $+60°$ C., preferably from $0°$ to $45°$ C. In general, the halogenation is carried out under normal pressure. However, it is also possible to carry out the halogenation under an increased pressure (for example in the pressure range from 1 to 50 bar).

Hydrogen halide is split off in the third reaction step in the presence of acid-binding agents.

Acid-binding agents which may be mentioned here are aliphatic, cycloaliphatic and aromatic tertiary amines. Examples of aliphatic groups which may be mentioned are straight-chain or branched lower alkyl groups with 1 to about 6 carbon atoms. Examples of cycloaliphatic groups which may be mentioned are the cyclopentyl and cyclohexyl radicals Examples of aromatic groups which may be mentioned are the phenyl, diphenyl and naphthyl radical. Examples of tertiary amines which may be mentioned are triethylamine, dimethylaniline and ethyldicyclohexylamine. It is also possible to use heterocyclic compounds, such as pyridine and quinoline. Furthermore, the hydroxides, carbonates, bicarbonates and acetates of alkali metals (for example sodium and potassium) and alkaline earth metals (for example magnesium and calcium) can also be used.

The acid-binding agent and the solvent are advantageously matched with one another. If tertiary amines are used, both polar and non-polar solvents are possible. The following solvents may be mentioned as examples here: methylene chloride, carbon tetrachloride, toluene, dimethylformamide, ethanol, acetone and tetrahydrofuran.

If metal salts are used, polar solvents, which may contain 50 to 100% by weight of water, are preferred.

The temperature in the reaction step according to the invention is in general in the range from $-20°$ C. to $80°$ C., preferably in the range from $-10°$ to $+40°$ C.

The reaction step can be carried out, for example, as follows:

The reaction components are brought together in solution and are stirred at the reaction temperature according to the invention until the reaction has ended. The end of the reaction can be detected by chromatographic methods. The products can be purified in the customary manner, for example by distillation, crystallization or column chromatography.

The nitriles prepared according to the invention can be hydrolysed to form the corresponding carboxamides and carboxylic acids.

For this purpose they are heated with an excess of concentrated acids such as hydrochloric acid, sulphuric acid or acetic acid.

If this reaction is carried out at temperatures from $60°$ C. to the refluxing temperature the carboxylic acids are formed after a relatively long reaction time (e.g. 2–10 h).

Under milder conditions (temperatures of about $40°$–$80°$ C., reaction time about 0.1–2 h) the carboxamides are formed. Here it may be appropriate to follow the progress of the reaction by means of, for example, thin layer chromatography, in order to terminate the hydrolysis, after the amide stage has been reacted.

The metal carboxylates are obtained from the carboxylic acids by reacting them with metal hydroxides and metal carbonates.

The halogenated sulphides according to the invention can be used as active compounds for combating microorganisms, in particular in industrial materials which may be attacked and decomposed by microorganisms.

According to the invention, industrial materials are non-living materials which have been prepared for use in industry. Examples of industrial materials which are to be preserved, by active compounds according to the invention, from microbial change or destruction can be adhesives, sizes, paper and card, textiles, leather, wood, paints and articles made of plastic, cooling lubricants and other materials which may be attacked and decomposed by microorganisms. Components of production plants, for example cooling water and paper machine circulations, which may be impaired by microorganisms, may also be mentioned in the context of the materials to be protected. Adhesives, sizes, paper, card, leather, wood, paints, cooling lubricants and water circulations, especially in the paper industry, may be mentioned as preferred industrial materials in the context of the present invention.

Examples which may be mentioned of microorganisms which can effect degradation of or a change in the industrial materials are bacteria, fungi, yeasts, algae and slime organisms. The substances according to the invention preferentially act on bacteria, moulds, in particular wood-discolouring and wood-destroying fungi (Basidiomycetes), slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicilium, such as *Penicillium, glaucum*, Polyporus, such as *Polyporus versicolor*, Aureobasidium, such as *Aureobasidium pullulans*, Sclerophoma, such as *Sclerophoma pityphila*, Staphylococcus, such as *Staphylococcus aureus*, Escherichia, such as *Escherichia coli*, and furthermore green algae, blue algae, brown algae and diatoms.

The active compounds according to the invention can be converted into the customary formulations, such as solutions, emulsions, suspensions, powders, pastes and granules, depending on their field of use.

These formulations can be prepared in a manner which is known per se, for example by mixing the active compounds with an extender, which consists of a liquid solvent and/or solid carrier, if appropriate using surface-active agents, such as emulsifiers and/or dispersing agents, it being possible, for example in the case of the use of aqueous extenders, for organic solvents, such as alcohols, optionally to be used as auxiliaries.

Organic solvents for the active compounds can be, for example, alcohols, such as lower aliphatic alcohols, preferably ethanol or isopropanol, or benzyl alcohols, ketones, such as acetone or methyl ethyl ketone, liquid hydrocarbons, such as benzine fractions, or halogenated hydrocarbons, such as 1,2-dichloroethane.

The use concentration of the active compounds according to the invention depends on the nature and occurrence of the microorganisms to be combated, and on the composition of the material to be protected. The optimum amount to be used can be determined by test series.

In general, the use concentrations are in the range from 0.001 to 5% by weight, preferably 0.005 to 0.5% by weight, based on the material to be protected.

The new active compounds according to the invention can also be in the form of a mixture with other known active compounds. The following active compounds may be mentioned as examples: benzyl alcohol mono(poly) hemiformal, benzimidazolyl methylcarbamates, tetramethylthiuram disulphide, zinc salts of dialkylthiocarbamates, 2,4,5,6-tetrachloroisophthalonitrile, thiazolylbenzimidazole, mercaptobenzothiazole, trialkyl-tin compounds, methylene-bisthiocyanates and phenol derivatives, such as 2-phenylphenol, (2,2'-dihydroxy-5,5'-dichloro)-diphenylmethane and 3-methyl-4-chloro-phenol, and quaternary ammonium salts.

PREPARATION EXAMPLES

EXAMPLE 1

70 g of bis-cyanoethyl sulphide were dissolved in 160 ml of methylene chloride. 135 g of sulphuryl chloride were added dropwise, first at $5°$ to $10°$ C. and then at $30°$ C. The mixture was then concentrated and the residue was washed with water and chromatographed on silica gel. After concentration and recrystallization from ethanol, 16 g of 1-chloro-2-cyanovinyl 2-cyano-ethyl sulphide of melting point $53°$ to $57°$ C. were obtained.

$^1$H-NMR: δ=2.6–2.9 (2H), 3.1–3.4 (2H) and 5.8 (1H).

EXAMPLE 2

23 g of 1,2-dichloro-2-cyano-vinyl 2-cyano-ethyl sulphide were obtained as an oil by the same route with 203 g of SO$_2$Cl$_2$.

$^1$H-NMR: δ=2.7–2.9 (2H) and 3.2–3.5 (2H).

EXAMPLE 3

11.8 g of 1-chloro-2-cyano-vinyl 2,2-dichloro-2-cyano-ethyl sulphide were obtained as an oil with 270 g of sulphuryl chloride by the same route, $^1$H-NMR: δ=3.9–4.1 (2H) and 5.8–6.0 (1H).

EXAMPLE 4

258 g of bis-cyanoethyl sulphide were dissolved in 0.9 liter of methylene chloride, and 938 g of potassium carbonate were added. 905 g of chlorine were passed in at 5° C. The mixture was then filtered, the filtrate was concentrated and the residue was chromatographed. 110 g of 1,2-dichloro-2-cyano-vinyl 2,2-dichloro-2-cyano-ethyl sulphide were obtained as an oil, $^1$H-NMR: δ=4.0–4.2.

EXAMPLE 5

133 g of 1,2-dichloro-2-cyano-vinyl 2,2-dichloro-2-cyano-ethyl sulphide were dissolved in 350 ml of tetrahydrofuran, and 53.6 g of triethylamine were added dropwise at 5° to 10° C. The triethylamine hydrochloride which had precipitated out was filtered off with suction, the filtrate was concentrated and the residue was distilled (boiling point 120° to 145° C./2.5 mbar). 66.3 g of 1,2-dichloro-2-cyano-vinyl 2-chloro-2-cyano-vinyl sulphide were obtained as an oil, $^1$H-NMR: δ=7.1–7.4. A pure stereoisomer of melting point 58° to 60° C. crystallized out, $^1$H-NMR: δ=7.1.

EXAMPLE 6

Solutions of 350 g of 2,3-dichloroacrylonitrile in 0.75 litre of methylene chloride and 241 g of sodium bicarbonate in 1.6 litres of water were combined. Hydrogen sulphide was passed in, with vigorous stirring, until the mixture was saturated, and the mixture was stirred at room temperature for 5 hours, saturated again with hydrogen sulphide and stirred for a further 12 hours. The organic phase was separated off and concentrated. 184 g of bis-(2-chloro-2-cyano-vinyl) sulphide remained as a crystalline substance of melting point 70° to 80° C., $^1$H-NMR: δ=7.2–7.6.

EXAMPLE 7

180 g of bis-(2-chloro-2-cyano-vinyl) sulphide were dissolved in 2.6 liters of chloroform, 180 g of potassium carbonate and 50 g of trioctylmethylammonium chloride (technical grade) were added and a slow stream of chlorine was passed through for 2 days. The solution was washed with water and concentrated. The oily residue contained the phase transfer catalyst and 282 g of bis-(1,2,2-trichloro-2-cyano-ethyl) sulphide, MS: m/e=344/346/348/350 (M+).

EXAMPLE 8

The residue from Example 7 was dissolved in 0.5 liter of methylene chloride, and 150 g of pyridine were added dropwise at 0° to 5° C. The mixture was stirred for a further 4 hours, washed with water and concentrated, the residue was taken up in toluene and the mixture was filtered over silica gel. The filtrate was concentrated and the residue was distilled (boiling point 165°–172° C./18 mbar). 81 g of bis-(1,2-dichloro-2-cyano-vinyl) sulphide were obtained as an oil.

IR: $\sqrt{}$C≡N=2220 and 2205 cm$^{-1}$.

MS: m/e=272/274/276/278 (M+).

On addition of light petrol (boiling range 40°–80° C.) to the oil, a pure stereoisomer crystallized out (melting point 87° C.).

EXAMPLE 8a 290 g of bis-(2-chloro-2-cyano-vinyl) sulphide were dissolved in 1 liter of methylene chloride, and 11.2 g of pyridine were added. A slow stream of chlorine was passed through at room temperature for 48 hours. The solution was washed with dilute hydrochloric acid and water and concentrated. Impurities were distilled out of the residue under 0.2 mbar at a bottom temperature of 100° C. 344.6 g of bis-(1,2-dichloro-2-cyano-vinyl) sulphide remained as an oil. On addition of light petrol (boiling range 40° to 80° C.), crystallization occurred. The crystals were a mixture of the three possible stereoisomers and had a melting point of 69° to 71° C.

EXAMPLE 9

3.3 g of 1,2-dichloro-2-cyano-vinyl 2-chloro-2-cyano-vinyl sulphide were dissolved in 20 ml of methylene chloride, 2 g of potassium carbonate were added, and 2.15 g of sulphuryl chloride in 10 ml of dichloroethane were added dropwise at room temperature. The mixture was stirred at 70° C. for 12 hours and filtered, the filtrate was washed with water and concentrated and the resulting oil was chromatographed. 1.7 g of bis-(1,2-dichloro-2-cyano-vinyl) sulphide were obtained as an oil, which was identical to the product from Example 8.

EXAMPLE 10

35 g of bis-cyanoethyl sulphide and 20 g of pyridine were dissolved in 0.5 litre of methylene chloride, and 138 g of potassium carbonate were added. 110 g of chlorine were then passed in, while cooling with ice. The mixture was allowed to come to room temperature and was stirred for 3 hours, during which a weak stream of chlorine was passed through. Finally, the mixture was warmed to 40° C. and further chlorine was passed in, until a total of 250 g of chlorine had been added. The mixture was filtered, the filtrate was washed with water and concentrated and the residue was distilled (boiling point 110° to 140° C./0.3 mbar). 10.6 g of a mixture of 1,2-dichloro-2-cyano-vinyl 2-chloro-2-cyano-vinyl sulphide and bis-(1,2-dichloro-2-cyano-vinyl) sulphide were obtained.

EXAMPLE 11

28 g of bis-cyanoethyl sulphide were dissolved in 50 ml of dichloroethane, and 110 g of potassium carbonate were added. 64 g of bromine were then added dropwise at 20° to 30° C. The mixture was stirred at 40° C. for 16 hours, a further 40 g of potassium carbonate were added and the mixture was stirred at 60° C. for 16 hours. The mixture was filtered, the filtrate was washed with water and concentrated and the residue was chromatographed. 5.5 g of 2-bromo-2-cyano-vinyl 2-cyano-ethyl sulphide were obtained as an oil, $^1$H-NMR: δ=2.6–3.0 (2H), 3.0–3.4 (2H) and 7.5–7.9 (1H).

EXAMPLE 12

17.3 g of 1-chloro-2-cyano-vinyl 2-cyano-ethyl sulphide were dissolved in 100 ml of dichloroethane, and 9.8 g of sodium acetate were added. 16 g of bromine were then added dropwise at 20° C. The organic phase was washed with water, concentrated and chromatographed. 10.2 g of 2-bromo-1-chloro-2-cyano-vinyl 2-cyano-ethyl sulphide were obtained as an oil, $^1$H-NMR: $\delta = 2.6$–2.9 (2H) and 3.1–3.5 (2H).

EXAMPLE 13

26 g of 1,2-dichloro-2-cyano-vinyl 2,2-dichloro-2-cyano-ethyl sulphide were heated at 50° C. with 80 ml of concentrated hydrochloric acid and 80 ml of acetic acid for 30 minutes. The mixture was concentrated, the residue was taken up in methylene chloride, the mixture was washed with sodium bicarbonate solution and the methylene chloride phase was dried and concentrated. 18 g of 2,2-dichloro-3(1,2-dichloro-2-cyano-vinyl)thiopropionic acid amide were obtained as a resinous oil, $^1$H-NMR: $\delta = 3.8$–4.2 (2H) and 6.5–7.3 (2H).

EXAMPLE 14

38.6 g of 1,2-dichloro-2-cyano-vinyl 2,2-dichloro-2-cyano-ethyl sulphide were heated at 70° C. with 116 ml of concentrated hydrochloric acid and 116 ml of acetic acid for 2.5 hours. The mixture was concentrated, the residue was taken up in methylene chloride and the mixture was washed with sodium bicarbonate solution. The aqueous solution was acidified with hydrochloric acid and extracted with methylene chloride. After the methylene chloride phase had been concentrated, 26.6 g of 2,2-dichloro-3(1,2-dichloro-2-cyano-vinyl)thio-propionic acid were obtained as a viscous oil, $^1$H-NMR: $\delta = 3.8$–4.2 (2H) and 9.7 (1H).

EXAMPLE 15

26.6 g of 2,2-dichloro-3(1,2-dichloro-2-cyano-vinyl)thiopropionic acid were suspended in 200 ml of water, and 7.6 g of sodium bicarbonate were added. The aqueous solution was washed with methylene chloride and concentrated. 28 g of the sodium salt were obtained, $^1$H-NMR: $\delta = 3.9$–4.2.

EXAMPLES 16 to 22

The following compounds were prepared according to Examples 13 to 15 and were characterised by nuclear magnetic resonance data:

| Example No. | Formula | $^1$H—NMR: $\delta =$ |
|---|---|---|
| 16 | $H_2N$—CO—$CCl_2$—$CH_2$—S—CCl=CH—CN | 3.8–4.2 (2H), 5.7–5.9 (1H), 6.5–7.2 (2H) |
| 17 | $H_2N$—CO—$CH_2$—$CH_2$—S—CCl=CH—CN | 2.4–2.9 (2H), 3.0–3.5 (2H), 5.7 (1H), 6.2–6.7 (2H) |
| 18 | $H_2N$—CO—$CH_2$—$CH_2$—S—CCl=CCl—CN | 2.4–2.8 (2H), 3.1–3.6 (2H), 5.5–6.5 (2H) |
| 19 | HOOC—$CH_2$—$CH_2$—S—CCl=CH—CN | 2.6–2.9 (2H), 3.0–3.5 (2H), 5.6–5.7 (1H), 10.7 (1H) |
| 20 | HOOC—$CH_2$—$CH_2$—S—CCl=CCl—CN | 2.6–2.9 (2H), 3.1–3.5 (2H), 11.3 (1H) |
| 21 | HOOC—$CCl_2$—$CH_2$—S—CCl=CH—CN | 3.9–4.1 (2H), 5.7–5.9 (1H), 9.7 (1H) |
| 22 | $Na^{\oplus}{}^{\ominus}$O—CO—$CCl_2$—$CH_2$—S—CCl=CH—CN | 4.0–4.2 (2H), 5.9–6.1 (1H), (CD$_3$OD) |

USE EXAMPLES

EXAMPLE 23

The minimum inhibitory concentrations (MIC) of active compounds according to the invention are determined to demonstrate the effectiveness against fungi:

Active compounds according to the invention are added in concentrations of 0.1 mg/liter to 5,000 mg/liter to an agar prepared from beerwort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which no growth at all of the species of microbes used takes place; it is shown in the following table.

α-Chloro-β-phenylsulphonyl acrylonitrile, which is used as a microbicide for the preservation of industrial material (DOS (German Published Specification) No. 2,500,265) is used as the comparison substance.

TABLE I

| | MIC value data in mg/liter for the action of substances according to the invention on fungi | | | | | | α-Chloro-β-phenylsulphonyl-acrylonitrile as the comparison substance |
|---|---|---|---|---|---|---|---|
| | Active compound according to Example | | | | | | |
| Test organisms | 3 | 5 | 4 | 8 | 2 | 9 | |
| Alternaria tenuis | 10 | 20 | 5 | 2 | | 0.75 | |
| Aspergillus niger | 20 | 2 | 10 | 2 | <20 | 2.5 | 50 |
| Aureobasidium pullulans | 10 | 5 | 5 | 1 | | 1 | |

TABLE I-continued

MIC value data in mg/liter for the action of substances according to the invention on fungi

| Test organisms | Active compound according to Example | | | | | | α-Chloro-β-phenylsulphonyl-acrylonitrile as the comparison substance |
|---|---|---|---|---|---|---|---|
| | 3 | 5 | 4 | 8 | 2 | 9 | |
| Chaetomium globosum | 15 | 2 | 10 | 2 | <20 | 2.5 | 50 |
| Coniophora puteana | 1 | <0.1 | 0.5 | <0.1 | | 0.5 | |
| Lentinus tigrinus | 5 | 0.5 | 2 | 0.5 | | 1 | |
| Penicillium glaucum | 20 | 1 | 10 | 1 | | 2.5 | 35 |
| Polyporus versicolor | 10 | 1 | 5 | .1 | | 1 | |
| Sclerophoma pityophila | 5 | 0.5 | 2 | 0.5 | 20 | 0.75 | |
| Trichoderma viride | 100 | 10 | 50 | 10 | | 10 | |

EXAMPLE 24

(Action against slime organisms)

Substances according to the invention are used in concentrations of in each case 0.1 to 100 mg/liter in Allen's nutrient solution (Arch. Mikrobiol. 17, 34 to 53 (1952)), which contains, in 4 liters of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam, dissolved in a little acetone. Shortly beforehand, the nutrient solution is infected with slime organisms (about 10⁶ germs/ml), which have been isolated from the spinning water circulations used in the production of polyamide. Nutrient solutions which contain the minimum inhibitory concentration (MIC) or higher concentrations of active compound are still completely clear after culture for 3 weeks at room temperature, that is to say the pronounced multiplication of the microbes and slime formation noticeable after 3 to 4 days in nutrient solutions containing no active compound are absent.

TABLE II

MIC values in mg/liter for the action of the substances shown below on slime organisms

| Active compound according to Example | MIC in mg/liter |
|---|---|
| 3 | 0.35 |
| 5 | 0.35 |
| 4 | 0.35 |
| 2 | 2 |
| 1 | 0.15 |

EXAMPLE 25

Action against bacteria

Active compounds according to the invention in concentrations of 1 to 5,000 mg/liter are added to an agar containing broth as the nutrient media. The nutrient medium is then infected in each case with the test organisms listed in Table III, and the infected medium is kept at 28° C. and 60 to 70% relative atmospheric humidity for 2 weeks. The MIC is the lowest concentration of active compound at which no growth at all of the species of microbe used takes place. The MIC values are shown in Table III.

TABLE III

MIC value data in mg/liter for the effect of the active compounds shown below on bacteria

| Test organisms | Active compound according to Example | | | | | | α-Chloro-phenyl-sulphonyl-acrylonitrile, as the comparison substance |
|---|---|---|---|---|---|---|---|
| | 3 | 5 | 4 | 8 | 2 | 9 | |
| Eschercihia coli | 200 | 20 | 50 | 50 | 200 | 25 | 200 |
| Staphylococcus aureus | 50 | 10 | 50 | <20 | 35 | 10 | 500 |

EXAMPLE 26

A mixed culture of green algae, blue algae, brown algae and diatoms (Stichococcus bacillaris Naegeli, Euglena gracilis Klebs, Chlorella pyrenoidosa Chick, Phormidium foveolarum Gomont, Oscillatoria geminata Meneghini and Phaedodactylum tricornutum Bohlin) is introduced into Allen's nutrient solution (Arch. Mikrobiol, 17, 34 to 53 (1952)), which contains, per 4 liters of sterile water, 0.2 g of ammonium chloride, 4.0 g of sodium nitrate, 1.0 g of dipotassium hydrogen phosphate, 0.2 g of calcium chloride, 2.05 g of magnesium sulphate and 0.02 g of iron chloride, while bubbling air through. After 2 weeks, the nutrient solution has been coloured a deep green-blue by intense algae growth. Dying off of the algae after addition of active compound according to the invention is recognized by the decolorization of the nutrient solution.

TABLE IV

Algae-destroying concentrations (mg/liter) of the substances listed below

| Active compounds according to Example | Destroying concentration in mg/liter |
|---|---|
| 3 | 25 |
| 5 | 25 |
| 4 | 25 |
| 2 | 50 |
| 1 | 100 |

EXAMPLE 27

Testing of 1,2-dichloro-2-cyano-vinyl 2-chloro-2-cyano-vinyl sulphide according to Example 5 as a preservative for cooling lubricants 1% of the active compound is added, as a preservative, to a cooling lubricant based on mineral oil.

5% strength use dilutions of the cooling lubricant are massively contaminated daily for 3 months with microbes (bacteria, yeasts and moulds) isolated from microbially decayed cooling lubricant use dilutions.

At the end of the testing period, the use dilutions are still free from germs; that is to say they are reliably preserved.

What is claimed is:

1. A halogenated sulphide of the formula

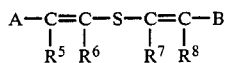

in which $R^5$ to $R^8$ are identical or different and denote hydrogen or halogen, at least one of the radicals $R^5$ to $R^8$ representing a halogen selected from the group consisting of chlorine, bromine and iodine and A and B are both nitrile.

2. A hologenated sulphide which is bis(2-chloro-2-cyano-vinyl)-sulphide.

3. A halogenated sulphide which is 1,2-dichloro-2-cyano-vinyl 2-chloro-2-cyano-vinyl sulphide.

4. A halogenated sulphide which is bis-(1,2-dichloro-2-cyano-vinyl)sulphide.